(12) United States Patent
Kikuno et al.

(10) Patent No.: US 9,320,660 B2
(45) Date of Patent: Apr. 26, 2016

(54) PROCESS FOR PRODUCTION OF WATER-ABSORBING RESIN PARTICLES, WATER-ABSORBING RESIN PARTICLES, WATER-STOPPING MATERIAL, AND ABSORBENT ARTICLE

(75) Inventors: Sachi Kikuno, Kurobe (JP); Atsushi Heguri, Himeji (JP); Masayoshi Handa, Himeji (JP); Nobuhiro Maeda, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 927 days.

(21) Appl. No.: 13/510,522

(22) PCT Filed: Nov. 24, 2010

(86) PCT No.: PCT/JP2010/070899
§ 371 (c)(1),
(2), (4) Date: Jul. 27, 2012

(87) PCT Pub. No.: WO2011/065368
PCT Pub. Date: Jun. 3, 2011

(65) Prior Publication Data
US 2012/0295103 A1    Nov. 22, 2012

(30) Foreign Application Priority Data
Nov. 27, 2009  (JP) .................. 2009-270419

(51) Int. Cl.
| | | |
|---|---|---|
| C08K 5/10 | (2006.01) | |
| C08F 2/44 | (2006.01) | |
| A61F 13/53 | (2006.01) | |
| A61F 13/15 | (2006.01) | |
| C08J 3/24 | (2006.01) | |
| C08F 2/32 | (2006.01) | |
| C08F 6/00 | (2006.01) | |

(52) U.S. Cl.
CPC ............ *A61F 13/53* (2013.01); *A61F 13/15658* (2013.01); *C08F 2/32* (2013.01); *C08F 6/008* (2013.01); *C08J 3/245* (2013.01); *C08F 2800/10* (2013.01); *C08F 2810/20* (2013.01); *C08J 2333/02* (2013.01); *Y10T 428/273* (2015.01); *Y10T 428/31855* (2015.04)

(58) Field of Classification Search
USPC ........................................................ 524/318
See application file for complete search history.

(56) References Cited

U.S. PATENT DOCUMENTS

| | | | |
|---|---|---|---|
| 4,340,706 A * | 7/1982 | Obayashi et al. ............. 526/207 |
| 4,497,930 A * | 2/1985 | Yamasaki et al. ............ 524/556 |
| 4,507,438 A * | 3/1985 | Obayashi et al. ............ 525/119 |
| 4,541,871 A | 9/1985 | Obayashi et al. | |
| 4,727,097 A | 2/1988 | Kobayashi et al. | |
| 4,755,560 A | 7/1988 | Ito et al. | |
| 2003/0153887 A1 | 8/2003 | Nawata et al. | |
| 2006/0194055 A1 | 8/2006 | Matsuda et al. | |
| 2007/0178786 A1 | 8/2007 | Nawata et al. | |
| 2008/0280154 A1 | 11/2008 | Kobushi et al. | |
| 2009/0281247 A1 | 11/2009 | Handa et al. | |

FOREIGN PATENT DOCUMENTS

| | | |
|---|---|---|
| CN | 1917954 | 2/2007 |
| CN | 101466740 | 6/2009 |
| DE | 4418818 | 1/1995 |
| EP | 0 036 463 | 9/1981 |
| EP | 0 083 022 | 7/1983 |
| EP | 0 176 664 | 4/1986 |
| EP | 1 291 368 | 3/2003 |
| EP | 1 609 810 | 12/2005 |
| EP | 1 721 663 | 11/2006 |
| EP | 2 387 981 | 11/2011 |
| EP | 2 631 251 | 8/2013 |
| GB | 2 126 591 | 3/1984 |
| JP | 56-131608 | 10/1981 |
| JP | 58-117222 | 7/1983 |
| JP | 59-062665 | 4/1984 |
| JP | 60-036534 | 2/1985 |
| JP | 60-255814 | 12/1985 |
| JP | 61-264006 | 11/1986 |
| JP | 3-195705 | 8/1991 |
| JP | 3-285918 | 12/1991 |
| JP | 4-045850 | 2/1992 |
| JP | 6-322179 | 11/1994 |
| JP | 7-026026 | 1/1995 |
| JP | 8-120013 | 5/1996 |
| JP | 8-157606 | 6/1996 |
| JP | 2001-040014 | 2/2001 |
| WO | 01/23479 | 4/2001 |
| WO | 02/085959 | 10/2002 |
| WO | 2004/083284 | 9/2004 |
| WO | 2006/123561 | 11/2006 |

* cited by examiner

*Primary Examiner* — Hui Chin
(74) *Attorney, Agent, or Firm* — Hamre, Schumann, Mueller & Larson, P.C.

(57) ABSTRACT

The present invention provides a method for producing water-absorbing resin particles having high equilibrium swelling capacity, a high water-absorption rate or high initial swelling capacity, and an appropriate particle size that achieves good handling performance; water-absorbing resin particles obtained by the method; and a water blocking material and an absorbent article which include the water-absorbing resin particles. The present invention is a method for producing water-absorbing resin particles, which comprises: preparing a hydrogel polymer by reversed-phase suspension polymerization of a water-soluble ethylenically unsaturated monomer in a hydrocarbon solvent in the absence of an internal crosslinking agent but in the presence of a surfactant with an HLB of 8 to 12; carrying out a post-crosslinking reaction of the hydrogel polymer whose moisture content is adjusted to 30 to 110 mass % based on a water-soluble ethylenically unsaturated monomer component that composes the hydrogel polymer.

9 Claims, 1 Drawing Sheet

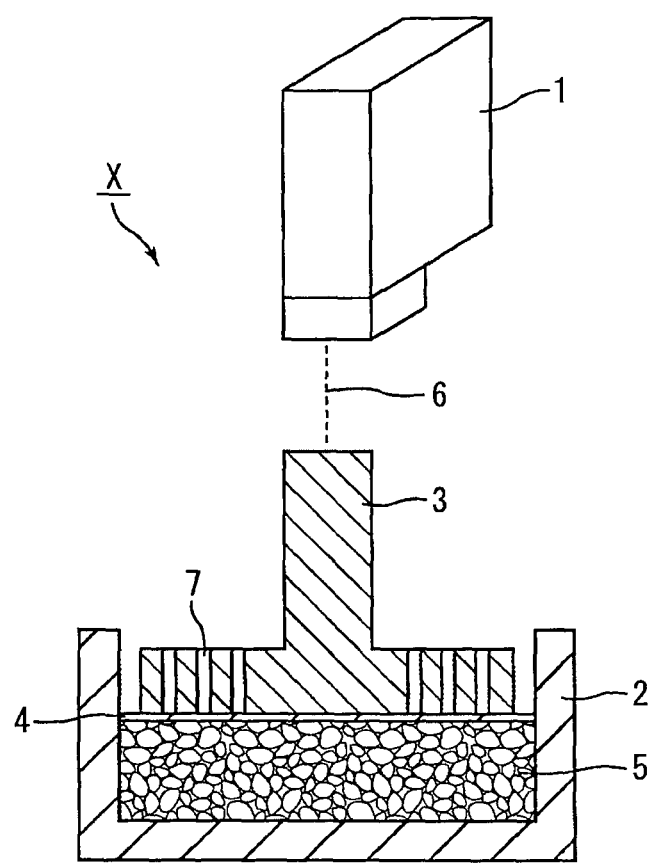

PROCESS FOR PRODUCTION OF WATER-ABSORBING RESIN PARTICLES, WATER-ABSORBING RESIN PARTICLES, WATER-STOPPING MATERIAL, AND ABSORBENT ARTICLE

TECHNICAL FIELD

The present invention relates to a method for producing water-absorbing resin particles, water-absorbing resin particles obtained by the method, a water blocking material, and an absorbent article. The present invention specifically relates to a method for producing, under specific production conditions, water-absorbing resin particles having high equilibrium swelling capacity, high initial swelling capacity or a high water-absorption rate, and an appropriate particle size that achieves excellent handling performance; water-absorbing resin particles with an excellent water blocking ability obtained by the method; and a water blocking material and an absorbent article which include the water-absorbing resin particles.

BACKGROUND ART

In recent years, water-absorbing resin particles have been widely used in various fields of, for example, hygienic articles such as disposable diaper and sanitary articles; agricultural and horticultural materials such as water-retaining materials and soil conditioners; and industrial and construction materials such as water blocking materials for cables and dewfall preventing materials. As the water-absorbing resin particles used in such fields, there have been known, for example, a hydrolyzed starch-acrylonitrile graft copolymer, a neutralized starch-acrylic acid graft copolymer, a saponified vinyl acetate-acrylic ester copolymer, and a partially neutralized polyacrylate. Generally, it has been desirable for water-absorbing resin particles to have high water absorption, an excellent water-absorption rate, high swelling capacity, and an appropriate median particle size in accordance with the uses.

Among these, water blocking materials for cables are formed of two or more liquid-permeable sheets and water-absorbing resin particles that are fixed between the sheets, if necessary using an adhesive and the like. The demand for such water blocking materials has increased with development of electrical industry and communication industry. Water blocking materials for cables are used to wrap the cores of cables such as power cables and optical communication cables, and thereby the cores are protected. Then, the outside of the water blocking materials is covered with materials such as rubber. Thus, cables are formed. If the outer materials of cables such as power cables and optical communication cables are deteriorated to produce cracks and moisture enters through the cracks and reaches the cores of the cables, reduction in electric power and communication noise may be caused. The water blocking materials prevent such problems. The water blocking materials absorb such moisture and swell to increase the pressure in the cables, and thereby moisture is prevented from reaching the cores of the cables.

It has been also desirable for a water-absorbing resin used as a water blocking material that is used for cables (e.g., power cables and optical communication cables) to have high absorption capacity of liquid with a high salt concentration such as seawater. In order to achieve such absorption capacity, the following methods are suggested: a method of polymerizing an amino group-containing water-soluble ethylenically unsaturated monomer with acrylic acid in the presence of a crosslinking agent (see Patent Literature 1); a method of mixing a water-absorbing resin with an anionic surfactant (see Patent Literature 2); and a method of coating the surfaces of water-absorbing polymer particles with a water soluble resin solution (see Patent Literature 3).

However, specific materials need to be used in these methods, which leads to an increase in production costs. Rather, use of a large amount of a conventional water-absorbing resin often reduces the costs of a water blocking material and improves the performance of a water blocking material. Therefore, such conventional methods have brought not so great effects to the industries.

Further, a water-absorbing resin used as a water blocking material needs to prevent water penetration from the outside owing to cable damage early and maintain a water blocking effect for a long time. In addition to these, the water-absorbing resin needs to be efficiently formed into a water blocking material and have excellent handling performance as powder in the production of the water blocking material. Therefore, in order to achieve such performances, water-absorbing resin particles used for a water blocking material need to have high swelling capacity, a high water-absorption rate, and an appropriate particle size that achieves good handling performance.

One way of improving swelling capacity of water-absorbing resin particles is to control crosslink density thereof. For example, the following methods are suggested. A method in which reversed-phase suspension polymerization of an acrylic acid/acrylate aqueous solution is carried out in the coexistence of a surfactant with an HLB of 8 to 12, a crosslinking agent is added thereto (immediately after the polymerization), and a crosslinking reaction is carried out (see Patent Literature 4); and a method in which a percentage of water content of a carboxyl group-containing polymer is set at 10 to 30 wt %, and a crosslinking reaction of the surface is started (see Patent Literature 5). However, even these methods do not achieve high swelling capacity that is needed for water-absorbing resin particles used for a water blocking material.

Therefore, a technology for producing water-absorbing resin particles having high equilibrium swelling capacity, a high water-absorption rate or high initial swelling capacity, and an appropriate particle size that achieves good handling performance is desirable.

CITATION LIST

Patent Literature

Patent Literature 1: Japanese Kokai Publication H04-45850 (JP-A H04-45850)
Patent Literature 2: Japanese Kokai Publication H06-322179 (JP-A H06-322179)
Patent Literature 3: Japanese Kokai Publication H03-285918 (JP-A H03-285918)
Patent Literature 4: Japanese Kokai Publication S56-131608 (JP-A S56-131608)
Patent Literature 5: Japanese Kokai Publication H03-195705 (JP-A H03-195705)

SUMMARY OF INVENTION

Technical Problem

An object of the present invention is to provide a method for producing water-absorbing resin particles having high equilibrium swelling capacity, a high water-absorption rate or high initial swelling capacity, and an appropriate particle size that achieves good handling performance; water-absorbing resin particles obtained by the method; and a water blocking material and an absorbent article which include the water-absorbing resin particles.

Solution to Problem

The present invention relates to the following method for producing water-absorbing resin particles, water-absorbing resin particles obtained by the method, a water blocking material and an absorbent article which include the water-absorbing resin particles.

That is, the present invention relates to:
1. a method for producing water-absorbing resin particles, which comprises: preparing a hydrogel polymer by reversed-phase suspension polymerization of a water-soluble ethylenically unsaturated monomer in a hydrocarbon solvent in the absence of an internal crosslinking agent but in the presence of a surfactant with an HLB of 8 to 12; carrying out a post-crosslinking reaction of the hydrogel polymer whose moisture content is adjusted to 30 to 110 mass % based on a water-soluble ethylenically unsaturated monomer component that composes the hydrogel polymer;
2. the method described in 1, wherein the surfactant with an HLB of 8 to 12 is at least one compound selected from the group consisting of sorbitan fatty acid esters, polyglycerin fatty acid esters, and sucrose fatty acid esters;
3. the method described in 1 or 2, wherein a post-crosslinking agent is a glycidyl ether compound;
4. the method described in 1, 2, or 3, wherein the amount of a post-crosslinking agent is 0.0001 to 1 mol % based on the total molar amount of the water-soluble ethylenically unsaturated monomer;
5. the method described in 1, 2, 3, or 4, wherein the amount of a post-crosslinking agent based on the total molar amount of the water-soluble ethylenically unsaturated monomer is in the range of the formula:

$$(-0.0002Z+0.023) \leq Y \leq (-0.0002Z+0.050) \quad (1)$$

wherein Y represents the amount (mol %) of the post-crosslinking agent, and Z represents the moisture content (mass %) of the hydrogel polymer that is mixed with the post-crosslinking agent;
6. water-absorbing resin particles obtained by the method described in 1, 2, 3, 4, or 5;
7. the water-absorbing resin particles described in 6, wherein equilibrium swelling capacity is 10 to 28 mm, a water-absorption rate is 1 to 20 seconds, and a median particle size is 80 to 400 µm;
8. an absorbent article, which comprises: a liquid-permeable sheet; a liquid-impermeable sheet; and an absorber sandwiched between the liquid-permeable sheet and the liquid-impermeable sheet, the absorber including the water-absorbing resin particles described in 6 or 7; and
9. a water blocking material, which comprises: two or more liquid-permeable sheets; and an absorber sandwiched with two or more sheets of the liquid-permeable sheets, the absorber including the water-absorbing resin particles described in 6 or 7 in an amount of 30 to 300 g/m².

The present invention is described in detail below.

The method for producing water-absorbing resin particles of the present invention includes preparing a hydrogel polymer by reversed-phase suspension polymerization of a water-soluble ethylenically unsaturated monomer in a hydrocarbon solvent in the absence of an internal crosslinking agent but in the presence of a surfactant with an HLB of 8 to 12.

Examples of the water-soluble ethylenically unsaturated monomer include (meth)acrylic acid ("acryl-" and "methacryl-" as used herein are collectively referred to as "(meth)acryl-", hereinafter the same applies), nonionic monomers such as 2-(meth)acrylamide-2-methylpropanesulfonic acid and/or an alkali salt thereof, (meth)acrylamide, N,N-dimethyl(meth)acrylamide, 2-hydroxyethyl(meth)acrylate, N-methylol(meth)acrylamide, and polyethylene glycol mono (meth)acrylate; amino group-containing unsaturated monomers such as N,N-diethylaminoethyl(meth)acrylate, N,N-diethylaminopropyl(meth)acrylate, and diethylaminopropyl (meth)acrylamide and quaternary salts thereof. At least one monomer selected from the group may be used. Among these, acrylic acid, methacrylic acid, or alkali salts thereof, acrylamide, methacrylamide, or N,N-dimethylacrylamide is preferably used because they are industrially available.

The water-soluble ethylenically unsaturated monomer may be usually used in the form of an aqueous solution. The concentration of the water-soluble ethylenically unsaturated monomer in the aqueous solution is preferably in the range of from 20 mass % to a concentration of the saturated aqueous solution. The concentration of the water-soluble ethylenically unsaturated monomer is more preferably 25 to 45 mass %, still more preferably 30 to 42 mass %, and particularly preferably 35 to 40 mass % because the state of W/O reversed-phase suspension is improved, particles with an appropriate particle size can be obtained, and swelling capacity of the resulting water-absorbing resin particles is improved.

When the water-soluble ethylenically unsaturated monomer is an acid group-containing monomer such as methacrylic acid and 2-(meth)acrylamide-2-methylpropanesulfonic acid, the acid radical of the monomer may be neutralized by an alkaline neutralizer such as an alkali metal salt. Examples of such an alkaline neutralizer include aqueous solutions of sodium hydroxide, potassium hydroxide, and ammonium hydroxide. Each example of the alkaline neutralizer may be used alone, or two or more of these may be used in combination.

The degree of neutralization of all the acid groups by the alkaline neutralizer is preferably in the range of from 10 to 100 mol %, more preferably in the range of from 30 to 90 mol %, still more preferably in the range of from 50 to 80 mol %, and particularly preferably in the range of from 65 to 78 mol % in order to increase osmotic pressure of the resulting water-absorbing resin particles, whereby their high swelling capacity is achieved, and to prevent disadvantages in safety or the like caused by the remaining excess alkaline neutralizer.

Examples of a radical polymerization initiator added to the aqueous solution of the water-soluble ethylenically unsaturated monomer include: persulfates such as potassium persulfate, ammonium persulfate, and sodium persulfate; peroxides such as methyl ethyl ketone peroxide, methyl isobutyl ketone peroxide, di-t-butyl peroxide, t-butylcumyl peroxide, t-butyl peroxyacetate, t-butyl peroxyisobutyrate, t-butyl peroxypivalate, and hydrogen peroxide; and azo compounds such as 2,2'-azobis[2-(N-phenylamidino)propane]dihydrochloride, 2,2'-azobis[2-(N-allylamidino)propane]dihydrochloride, 2,2'-azobis{2-[1-(2-hydroxyethyl)-2-imidazoline-2-yl]propane}dihydrochloride, 2,2'-azobis{2-methyl-N-[1,1-bis(hydroxymethyl)-2-hydroxyethyl]propioneamide}, 2,2'-azobis[2-methyl-N-(2-hydroxyethyl)-propioneamide], and 4,4'-azobis(4-cyano valeric acid). Each of these radical polymerization initiators may be used alone, or two or more of these may be used in combination.

The radical polymerization initiator is usually added in an amount of from 0.005 to 1 mol % based on the total molar amount of the water-soluble ethylenically unsaturated monomer. An amount less than 0.005 mol % of the radical polymerization initiator is not preferred because the polymerization reaction takes a large amount of time. An amount of the initiator exceeding 1 mol % is not preferred because the polymerization reaction rapidly occurs.

The radical polymerization initiator may be also used as a redox polymerization initiator together with a reducing agent such as sodium sulfite, sodium hydrogen sulfite, ferrous sulfate, and L-ascorbic acid.

In addition, in order to control swelling capacity of the water-absorbing resin particles, a chain transfer agent may be added. Examples of the chain transfer agent include hypophosphites, thiols, thiolic acids, secondary alcohols, and amines.

The method for producing water-absorbing resin particles of the present invention includes reversed-phase suspension polymerization in the absence of an internal crosslinking agent but in the presence of a surfactant with an HLB of 8 to 12.

In aqueous polymerization, swelling capacity, especially equilibrium swelling capacity, of the water-absorbing resin particles may be improved through a polymerization reaction in the absence of an internal crosslinking agent. However, the hydrogel polymer resulting from the polymerization is too viscous to be cut, which considerably increases a load on the subsequent drying process and crushing process. Therefore, water-absorbing resin particles having good swelling capacity and an appropriate particle size are difficult to be obtained.

In the conventional reversed-phase suspension polymerization, a hydrogel polymer can be obtained without using an internal crosslinking agent at the time of the polymerization reaction, but some aggregated substances tend to be generated or particles tend to be adhered to one another to be flocculated.

As a result of intensive investigations by the present inventors, it has been found that particles suitable for a water blocking material can be simply obtained by reversed-phase suspension polymerization of a water-soluble ethylenically unsaturated monomer in an aqueous solution using a specific surfactant and a hydrocarbon solvent. In addition, a post-crosslinking reaction of the particles is carried out, and thereby high-performance water-absorbing resin particles suitable for a water blocking material can be obtained. Thus, the present invention has been completed.

The "internal crosslinking agent" in the present invention refers to a compound contributing to form a cross-linked structure between high polymer chains during polymerization of a monomer. The "internal crosslinking agent" specifically refers to, for example, a compound having, in the molecule, two or more polymerizable unsaturated groups that are polymerizable with the water-soluble ethylenically unsaturated monomer, or a compound having, in the molecule, two or more functional groups that can react with a functional group (for example, a carboxyl group when the water-soluble ethylenically unsaturated monomer is acrylic acid) included in the water-soluble ethylenically unsaturated monomer.

In the present invention, a surfactant with an HLB of 8 to 12 is used. Use of the surfactant with an HLB of 8 to 12 improves the state of the W/O reversed-phase suspension and provides particles with an appropriate particle size. The HLB of the surfactant is preferably 8.5 to 10.5.

Examples of the surfactant includes nonionic surfactants such as sorbitan fatty acid esters, (poly)glycerin fatty acid esters, (the expression "(poly)" indicates both a case in which the prefix "poly" is placed before the term and a case in which "poly" is not placed before the term, hereinafter the same applies), sucrose fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallylformaldehyde condensed polyoxyethylene ethers, polyoxyethylene polyoxypropylene block copolymers, polyoxyethylene polyoxypropyl alkyl ethers, and polyethylene glycol fatty acid esters; and anionic surfactants such as fatty acid salts, alkylbenzene sulfonates, alkyl methyl taurates, polyoxyethylene alkyl phenyl ether sulfates, polyoxyethylene alkyl ether sulfonates, polyoxyethylene alkyl ether phosphates, and polyoxyethylene alkyl allyl ether phosphates. Among these, sorbitan fatty acid esters, polyglycerine fatty acid esters, and sucrose fatty acid esters are preferred because they improve the state of the W/O reversed-phase suspension and provide particles with a particle size suitable for a water blocking material, and they are industrially available. Among these, sorbitan fatty acid esters are more preferred because the resulting water-absorbing resin particles have high swelling capacity. Each of these surfactants may be used alone, or two or more of these may be used in combination.

In the present invention, polymer protective colloid may be used together with the surfactant in order to stabilize the state of the W/O reversed-phase suspension. Examples of the polymer protective colloid include maleic anhydride-modified polyethylene, maleic anhydride-modified polypropylene, maleic anhydride-modified ethylene-propylene copolymer, maleic anhydride-modified EPDN (ethylene-propylene-diene-terpolymer), maleic anhydride-modified polybutadiene, ethylene-maleic anhydride copolymer, ethylene-propylene-maleic anhydride copolymer, butadiene-maleic anhydride copolymer, oxidized polyethylene, ethylene-acrylic acid copolymer, ethyl cellulose, and ethyl hydroxyethyl cellulose. Among these, maleic anhydride-modified polyethylene, maleic anhydride-modified polypropylene, maleic anhydride-modified ethylene-propylene copolymer, oxidized polyethylene, and ethylene-acrylic acid copolymer are preferred in view of stability of the W/O reversed-phase suspension. Each of these polymer protective colloids may be used alone, or two or more of these may be used in combination.

In order to stabilize the state of the W/O reversed-phase suspension and select the efficient amount for a suspension stabilization effect, the amount of the surfactant is preferably 0.1 to 5 parts by mass, more preferably 0.2 to 3 parts by mass, and still more preferably 0.4 to 2 parts by mass, based on 100 parts by mass of the aqueous solution of the water-soluble ethylenically unsaturated monomer which is to be subjected to reversed-phase suspension polymerization.

Examples of the hydrocarbon solvent include aliphatic hydrocarbons such as n-hexane, n-heptane, and ligroin; alicyclic hydrocarbons such as cyclopentane, methylcyclopentane, cyclohexane, and methylcyclohexane; and aromatic hydrocarbons such as benzene, toluene, and xylene. Each of these may be used alone, or two or more of these may be used in combination. Among these, n-hexane, n-heptane, and cyclohexane are preferred because they are industrially available. Particularly, n-heptane is more preferred because the state of the W/O reversed-phase suspension of the present invention is improved, particles with a particle size suitable for a water blocking material are easily provided, and the resulting water-absorbing resin particles have good swelling capacity.

In order to appropriately remove heat of the polymerization to make the polymerization temperature easy to control, the amount of the hydrocarbon solvent is preferably 50 to 600 parts by mass and more preferably 100 to 550 parts by mass, based on 100 parts by mass of the water-soluble ethylenically unsaturated monomer which is to be subjected to reversed-phase suspension polymerization.

In the present invention, the reaction temperature of the reversed-phase suspension polymerization differs depending on the kind of the water-soluble radical polymerization initiator to be used, and therefore cannot be unconditionally determined. Generally, the reaction temperature is preferably 20° C. to 110° C. and more preferably 40° C. to 90° C. in order to shorten the polymerization time by allowing the polymerization to rapidly proceed, easily remove the heat of the polymerization, and allow the reaction to proceed smoothly. The reaction time is generally 0.5 to 4 hours.

Generally, the water-absorbing resin particles obtained by the reversed-phase suspension polymerization and their precursor (hydrogel polymer) are formed into various forms. For example, they are formed into a spherical shape, granules, debris, or a konpeito shape, or formed as coagulations thereof. In the present invention, the hydrogel polymer is preferably formed into granules because the particles are less likely to be flocculated by adhering, and the particles can be simply obtained in a form suitable for the water blocking material. The granules preferably have uniform irregularities on their surface.

In the method for producing water-absorbing resin particles of the present invention, a post-crosslinking reaction of the hydrogel polymer is subsequently carried out after the moisture content of the hydrogel polymer is adjusted to 30 to 110 mass % based on the water-soluble ethylenically unsaturated monomer component that composes the hydrogel polymer.

Examples of the method (hereinafter, also referred to as the first drying) for adjusting the moisture content of the hydrogel polymer to 30 to 110 mass % based on the water-soluble ethylenically unsaturated monomer component that composes the hydrogel polymer include, but are not particularly limited to: a method of removing water by azeotropic distillation of a solution of the hydrogel polymer dispersed in a hydrocarbon solvent by heating from the outside; a method of low pressure drying a hydrogel polymer that is obtained by decantation; and a method of low pressure drying a hydrogel polymer that is separated using a filter. Among these, removing water by azeotropic distillation of a solution of the hydrogel polymer dispersed in a hydrocarbon solvent is preferred in view of its simple production process.

The post-crosslinking reaction is carried out after the first drying. The post-crosslinking reaction of the hydrogel polymer that is obtained as described above is carried out under the specific conditions. Thereby, water-absorbing resin particles with excellent swelling capacity are prepared.

The post-crosslinking agent is a compound having, in the molecule, two or more functional groups that can react with a functional group (for example, a carboxyl group when the water-soluble ethylenically unsaturated monomer is acrylic acid) included in the water-soluble ethylenically unsaturated monomer. The post-crosslinking agent is preferably a water-soluble compound such as polyols, e.g., ethylene glycol, propylene glycol, 1,4-butanediol, trimethylol propane, glycerin, polyoxyethylene glycol, polyoxypropylene glycol, and polyglycerine; glycidyl ether compounds such as (poly)ethylene glycol diglycidyl ether, (poly)propylene glycol diglycidyl ether, and (poly)glycerin diglycidyl ether; haloepoxy compounds such as epichlorohydrin, epibromhydrin, and α-methyl epichlorohydrin; compounds having two or more reactive functional groups such as isocyanate compounds such as 2,4-tolylenediisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Each of these may be used alone, or two or more of these may be used in combination.

Among these, glycidyl ether compounds are preferred in view of their excellent reactivity. Among the glycidyl ether compounds, ethylene glycol diglycidyl ether, propylene glycol diglycidyl ether, glycerin diglycidyl ether, polyethylene glycol diglycidyl ether, and polyglycerol glycidyl ether are more preferred in view of their high water solubility and good handling performance as the post-crosslinking agent. Ethylene glycol diglycidyl ether and propylene glycol diglycidyl ether are still more preferred in view of high swelling capacity of the resulting water-absorbing resin particles.

The amount of the post-crosslinking agent based on the total molar amount of the water-soluble ethylenically unsaturated monomer that composes the hydrogel polymer is preferably 0.0001 to 1 mol %, more preferably 0.0005 to 0.5 mol %, still more preferably 0.001 to 0.1 mol %, and particularly preferably 0.005 to 0.05 mol %. If the amount of the post-crosslinking agent based on the total molar amount of the water-soluble ethylenically unsaturated monomer is less than 0.0001 mol %, the water-absorbing resin particles are weakly cross-linked and the surfaces of the particles tend to be viscous when the particles absorb water and the initial swelling capacity tends to be low. If the amount exceeds 1 mol %, the particles are excessively cross-linked to one another, which results in low equilibrium swelling capacity.

The total molar amount of the water-soluble ethylenically unsaturated monomer component that composes the hydrogel polymer equals to the sum of the molar amounts of the water-soluble ethylenically unsaturated monomers used in the polymerization reaction.

In the present invention, mixing of the hydrogel polymer with the post-crosslinking agent is performed after adjusting the moisture content of the hydrogel polymer to a specific range. Thus, the moisture content of the hydrogel polymer at the time of mixing the hydrogel polymer with the post-crosslinking agent is controlled, which allows the post-crosslinking reaction to more suitably proceed.

The moisture content of the hydrogel polymer in the post-crosslinking process is 30 to 110 mass %, preferably 35 to 105 mass %, more preferably 40 to 100 mass %, still more preferably 45 to 95 mass %, particularly preferably 50 to 90 mass %, and most preferably 55 to 85 mass %, based on the water-soluble ethylenically unsaturated monomer component that composes the hydrogel polymer. Such a moisture content in the above range shortens the time of the first drying process, improves the efficiency of the first drying process, and maximally improves swelling capacity obtained by the post-crosslinking reaction.

The moisture content may be determined as follows: the amount of moisture in the hydrogel polymer is determined as the sum of the amount of moisture, which is used if needed when the post-crosslinking agent is added, and the amount of moisture (amount of moisture of the first-dried gel) obtained by subtracting the amount of moisture removed out in the first drying process from the amount of moisture in an aqueous monomer solution before polymerization; and the ratio of the resulting amount of moisture in the hydrogel polymer to the mass of the water-soluble ethylenically unsaturated monomer component that composes the hydrogel polymer is determined.

The mass of the water-soluble ethylenically unsaturated monomer component that composes the hydrogel polymer may be determined as a theoretical polymer solid content from the total mass of the water-soluble ethylenically unsaturated monomer that is used for the polymerization reaction.

The ratio of the moisture content of the first-dried gel relative to the moisture amount added if needed, when the post-crosslinking agent is added, is preferably from 100:0 to 60:40, more preferably from 99:1 to 70:30, still more preferably from 98:2 to 80:20, and further more preferably from 98:2 to 90:10, from a stand point of rationally improving economic efficiency of the process by shortening the drying process and simultaneously, dispersing the post-crosslinking agent uniformly.

According to the present invention, in order to give water-absorbing resin particles with high swelling capacity, the amount of the post-crosslinking agent based on the total molar amount of the water-soluble ethylenically unsaturated monomer is preferably in the range of the following formula (1), more preferably in the range of the following formula (2), and still more preferably in the range of the following formula (3).

$$(-0.0002Z+0.023) \leq Y \leq (-0.0002Z+0.050) \quad (1)$$

$$(-0.0002Z+0.025) \leq Y \leq (-0.0002Z+0.046) \quad (2)$$

$$(-0.0002Z+0.027) \leq Y \leq (-0.0002Z+0.042) \quad (3)$$

In the formulae (1) to (3), Y represents the amount (mol %) of the post-crosslinking agent and Z represents the moisture content (mass %) of the hydrogel polymer at the post-crosslinking process.

When the hydrogel polymer is mixed with the post-crosslinking agent, water or a hydrophilic organic solvent may be used as a solvent in order to allow the post-crosslinking agent to uniformly disperse. Examples of the hydrophilic organic solvent include lower alcohols such as methyl alcohol, ethyl alcohol, and isopropyl alcohol; ketones such as acetone and methyl ethyl ketone; ethers such as dioxane and tetrahydrofuran; amides such as N,N-dimethylformamide; and sulfoxides such as dimethyl sulfoxide. Each of these may be used alone or if necessary with water, or two or more of these may be used in combination.

The reaction temperature during the crosslinking reaction of the water-absorbing resin with the post-crosslinking agent is 60° C. or higher, preferably 70° C. to 200° C., and more preferably 80° C. to 150° C. If the reaction temperature is lower than 60° C., the crosslinking reaction is less likely to proceed and takes a long time. If the reaction temperature exceeds 200° C., the resulting water-absorbing resin particles tend to be deteriorated and water absorption capacity thereof tends to be reduced.

The reaction time of the post crosslinking differs depending on the reaction temperature, the kind and amount of the post-crosslinking agent, and therefore can not be unconditionally determined. Generally, the reaction time is 1 to 300 minutes and preferably 5 to 200 minutes.

Although the reason why the water-absorbing resin particles having high swelling capacity are obtained according to the method of the present invention is not understood, the following reason is considered: the best balance between the crosslink density near the surfaces of the water-absorbing resin particles and the crosslink density of the inner portions of the water-absorbing resin particles is provided by preparing the hydrogel polymer with an appropriate particle size in the absence of an internal crosslinking agent, adjusting the moisture content of the hydrogel polymer to a specific range, and carrying out a post-crosslinking reaction of the resulting hydrogel polymer under the specific conditions.

In the present invention, a drying process (hereinafter, referred to as the second drying) may be performed after the post-crosslinking reaction as follows: the solvent such as water and an organic solvent is distilled off by the application of energy such as heat from the outside. Powdered water-absorbing resin particles are prepared through such second drying.

Examples of the method for the second drying include, but are not limited to, a method of removing water and a hydrocarbon solvent at the same time by distillation from the mixture of the hydrocarbon solvent and the post-crosslinked resin particles dispersed in the solvent; a method of low pressure drying resin particles that are obtained by decantation; and a method of low pressure drying resin particles that are separated using a filter. Among these, the method of removing water and a hydrocarbon solvent at the same time by distillation from the mixture of the hydrocarbon solvent and the post-crosslinked resin particles that are dispersed in the solvent is preferred in view of the simple production process.

The method for producing the water-absorbing resin particles of the present invention can provide the water-absorbing resin particles having high equilibrium swelling capacity, a high water-absorption rate and high initial swelling capacity, and an appropriate particle size that achieves good handling performance. Such water-absorbing resin particles are also one aspect of the present invention.

The water-absorbing resin particles of the present invention preferably have equilibrium swelling capacity (value after 10 minutes) of 10 to 28 mm. Such high swelling capacity of the water-absorbing resin particles prevents initial water penetration through a crack of an external material of a cable, achieves a long time water blocking effect, and provides appropriate pressure due to the swollen resin particles, but enough to prevent deterioration of the material of a cable. The equilibrium swelling capacity is more preferably 11 to 24 mm, still more preferably 12 to 20 mm, and particularly preferably 13 to 18 mm.

The water-absorbing resin particles of the present invention preferably have an absorption rate of physiological saline of 1 to 20 seconds. Such an excellent absorption rate can prevent water penetration through a crack of a cable more early. The water-absorption rate is more preferably 1 to 15 seconds and still more preferably 2 to 10 seconds.

The water-absorbing resin particles of the present invention preferably have a median particle size of 80 to 400 μm. The water-absorbing resin particles having such a median particle size can be formed into a thin water blocking material with good handling performance as powder. The median particle size is preferably 100 to 350 μm, more preferably 120 to 300 μm, and still more preferably 130 to 250 μm.

The ratio of the initial swelling capacity (after 1 minute) of the water-absorbing resin particles of the present invention to the equilibrium swelling capacity (value after 10 minutes) is preferably 70 to 100%, more preferably 80 to 100%, and still more preferably 85 to 100%.

The physiological saline absorption of the water-absorbing resin particles of the present invention is not Particularly limited, but the water-absorbing resin particles preferably absorb more physiological saline. The absorption is preferably 35 to 80 g/g, more preferably 45 to 75 g/g, and still more preferably 55 to 70 gig.

The initial swelling capacity (value after 1 minute), equilibrium swelling capacity (value after 10 minutes), a physiological saline-absorption rate, physiological saline absorption, and a median particle size, of the water-absorbing resin particles of the present invention are determined by the measurement methods described in the following Examples. The measurement method of swelling capacity of the present invention sufficiently accurately reproduces even a difference as small as about 1 mm. Therefore, such a measurement method is preferred to confirm a difference in swelling capacity of the water-absorbing resin particles depending on the production methods, and is widely used for evaluation of the water-absorbing resin particles that are used for a water blocking material.

Additives such as a heat-resistant stabilizer, an antioxidant, and an antibacteria agent may be added to the water-absorbing resin particles of the present invention in accordance with the intended use.

The amount of each additive differs depending on the use of the water-absorbing resin particles and the kind of the additive, but is preferably 0.001 to 10 parts by mass, more preferably 0.01 to 5 parts by mass, and still more preferably 0.1 to 2 parts by mass, based on the total mass of 100 parts by mass of the water-soluble ethylenically unsaturated monomer that composes the water-absorbing resin particles.

The total mass of the water-soluble ethylenically unsaturated monomer component that composes the water-absorbing resin particles may be determined as a theoretical polymer solid content from the total mass of the water-soluble ethylenically unsaturated monomer used for a polymerization reaction.

An absorbent article may be formed by a liquid-permeable sheet, a liquid-impermeable sheet, and an absorber sandwiched between the liquid-permeable sheet and the liquid-impermeable sheet. The absorber includes the water-absorbing resin particles of the present invention. Such an absorbent article is also another aspect of the present invention. Examples of the absorbent article of the present invention include disposable diapers, incontinence pads, sanitary articles, pet sheets, drip sheets for foods, and water blocking agents for power cables.

If the absorbent article of the present invention is used for a product in contact with skins, the liquid-permeable sheet is disposed on the side in contact with skins, and the liquid-impermeable sheet is disposed on a side opposite to the side in contact with skins.

Examples of the liquid-permeable sheet include a nonwoven fabric comprising a synthetic resin such as polyethylene, polypropylene, polyester, and polyamide; and a porous synthetic resin sheet. Examples of the liquid-impermeable sheet include a film comprising a synthetic resin such as polyethylene, polypropylene, and polyvinyl chloride and a sheet comprising a composite material including the synthetic resin and a nonwoven fabric.

The absorber including the water-absorbing resin particles of the present invention has a structure in which, for example, a laminate including the water-absorbing resin particles and hydrophilic fibers is wrapped with a permeable sheet such as tissue, or a nonwoven fabric, or a laminate including hydrophilic fibers stacked in a sheet-like structure and the water-absorbing resin particles dispersed between the hydrophilic fibers is wrapped with a permeable sheet such as tissue or a nonwoven fabric. Examples of the hydrophilic fiber include: cellulose fibers such as cotton pulp and chemical pulp; and artificial cellulose fibers such as rayon and acetate.

As one example of the absorbent article according to the present invention, a water blocking material is described below.

The water blocking material can be formed by two or more liquid-permeable sheets; and an absorber sandwiched with two or more sheets of the liquid-permeable sheets. The absorber includes the water-absorbing resin particles of the present invention in an amount of 30 to 300 $g/m^2$.

The water blocking material of the present invention specifically has, for example, a sheet-like structure in which the water-absorbing resin particles are fixed to a liquid-permeable sheet using an adhesive. The water blocking material of the present invention is used to wrap the core of a cable such as a power cable and an optical communication cable, and absorbs moisture entering through a crack that is created due to the deterioration of the outer material. Further, the swollen water blocking material increases the pressure in the cable, and thereby moisture is prevented from reaching the core of the cable.

The water blocking material of the present invention preferably includes the water-absorbing resin particles of the present invention in an amount of 30 to 300 $g/m^2$ and more preferably 100 to 250 $g/m^2$.

The same sheet as that used in the absorbent article is used as the liquid-permeable sheet. Examples of the adhesive include: adhesives base on rubber such as natural rubber, butyl rubber, and polyisoprene; adhesives including styrene elastomer such as a styrene-isoprene block copolymer (SIS) and a styrene-butadiene block copolymer (SBS); an ethylene-vinylacetate copolymer (EVA) adhesive; an adhesive including an ethylene-acrylic acid derivative copolymer such as an ethylene-ethyl acrylate copolymer (EEA); an ethylene-acrylic acid copolymer (EAA) adhesive; adhesives including a polyamide such as copolymerized nylon; adhesives including a polyolefin such as polyethylene and polypropylene; adhesives including polyester such as polyethylene terephthalate (PET) and copolymerized polyester; and acrylic adhesives.

Advantageous Effects of Invention

The present invention can provide a method for producing water-absorbing resin particles having high equilibrium swelling capacity, a high water-absorption rate or high initial swelling capacity, and an appropriate particle size that achieves good handling performance; water-absorbing resin particles obtained by the method; and a water blocking material and an absorbent article which include the water-absorbing resin particles.

BRIEF DESCRIPTION OF DRAWINGS

FIG. 1 is a schematic explanation view of a swelling capacity measuring apparatus.

DESCRIPTION OF EMBODIMENTS

The present invention is described below in more detail with reference to Examples, but is not limited only to these Examples.

Example 1

A cylindrical round bottomed separable flask having an internal diameter of 100 mm, equipped with a reflux condenser, a dropping funnel, a nitrogen gas inlet tube, and a stirring blade (which is coated with a fluororesin) having two-step four pitched paddle blades having a blade diameter of 50 mm as a stirrer was prepared. This flask was charged with 550 mL of n-heptane, and then 0.84 g of sorbitan monolaurate (Nonion LP-20R manufactured by Nippon Oil & Fats Co., Ltd.) having an HLB of 8.6 was added thereto as a surfactant. The contents were heated to 50° C. to dissolve the surfactant, and thereafter the contents were cooled to 40° C.

A 500-mL Erlenmeyer flask was charged with 70 g (0.783 mol) of an 80.5 mass % aqueous solution of acrylic acid, and then 112.3 g of a 20.9 mass % aqueous solution of sodium hydroxide was added dropwise thereto with cooling with ice to neutralize 75 mol % of the acrylic acid. Thereafter, 0.084 g of potassium persulfate was dissolved therein to prepare an aqueous monomer solution. The aqueous monomer solution has 69.3 g of a solids content equivalent to the polymer and 113 g of a moisture content.

Setting the rotational speed of the stirrer at 800 rpm, the resulting aqueous monomer solution was added to the separable flask. The air in the system was purged with nitrogen for 30 minutes. Thereafter, the flask was immersed in a water bath set at 70° C. to increase the temperature. The polymerization reaction was carried out for 2 hours to give a hydrogel polymer.

Subsequently, the temperature was increased using an oil bath to 120° C. and 78.4 g of water was distilled off from the system by azeotropic distillation of water and n-heptan with reflux of n-heptan. Thereafter, 1.40 g (0.00016 mol) of a 2% aqueous solution of ethylene glycol diglycidyl ether was added thereto (first drying process). At this time, the amount of moisture was 1.37 g, and the moisture content (based on polymer solid content) was 52 mass % based on the water-soluble ethylenically unsaturated monomer component constituting the hydrogel polymer. A mixture of the hydrogel polymer with a post-crosslinking agent was prepared, and the mixture was kept at 80° C. for 2 hours.

Then, the mixture was dried by evaporation of the n-heptane (second drying process) to give 72.1 g of granular water-absorbing resin particles.

Examples 2 to 4

The same operations as in Example 1 were performed to give 72.8 g, 72.7 g, and 73.1 g of granular water-absorbing resin particles, except that the amount of water distilled off from the system in the first drying process was changed to 74.9 g, 64.5 g, and 81.8 g; the amount of the 2% aqueous solution of ethylene glycol diglycidyl ether was changed to 1.05 g (0.00012 mol), 0.7 g (0.00008 mol), and 1.75 g (0.0002 mol); and the moisture content (based on polymer solid content) was changed to 57 mass %, 71 mass %, and 48 mass %, respectively.

Example 5

Granular water-absorbing resin particles were obtained in the same manner as in Example 1, except that the amount of water distilled off from the system in the first drying process was changed to 81.8 g; the 2% aqueous solution of ethylene glycol diglycidyl ether was changed to 2.47 g (0.00019 mol) of a 2% aqueous solution of polyglycerol glycidyl ether; and the moisture content (based on polymer solid content) was changed to 49 mass %. The yield of the resin particles was 72.4 g.

Example 6

Granular water-absorbing resin particles were obtained in the same manner as in Example 1, except that 1.40 g of diglycerin monolaurate (POEM DL-100 manufactured by Riken Vitamin Co., Ltd.) having an HLB of 9.4 was added as a surfactant. The yield of the resin particles was 70.8 g.

Example 7

Granular water-absorbing resin particles were obtained in the same manner as in Example 1, except that 1.75 g of sucrose stearate (S-970 manufactured by Mitsubishi-Kagaku Foods Corporation) having an HLB of 9 was added as a surfactant. The yield of the resin particles was 71.1 g.

Example 8

Flocculated granular water-absorbing resin particles were obtained in the same manner as in Example 1, except that 0.02 g of an amorphous silica powder (TOKUSIL P manufactured by Tokuyama Corporation) was added to the polymerization solution after the completion of the polymerization. The yield of the resin particles was 73.2 g.

Comparative Example 1

Granular water-absorbing resin particles were obtained in the same manner as in Example 1, except that the amount of water distilled off from the system in the first drying process was changed to 97.8 g; the amount of the 2% aqueous solution of ethylene glycol diglycidyl ether was changed to 4.2 g (0.00048 mol); and the moisture content (based on polymer solid content) was changed to 28 mass %. The yield of the resin particles was 71.8 g.

Comparative Example 2

A 500-mL four-necked round bottomed flask equipped with a stirrer, a reflux condenser, a dropping funnel, and a nitrogen gas inlet tube was charged with 213 g of cyclohexane, and then 1.9 g of sorbitan monolaurate (Nonion LP-20R manufactured by Nippon Oil & Fats Co., Ltd.) having an HLB of 8.6 was added thereto. The surfactant was dissolved with stirring at room temperature, and dissolved oxygen was purged by bubbling of nitrogen gas.

A 200-mL Erlenmeyer flask was charged with 48.8 g (0.542 mol) of an 80 mass % aqueous solution of acrylic acid, and 67.0 g of a 25.9 mass % aqueous solution of sodium hydroxide was added dropwise thereto with cooling from the outside to neutralize 80 mol % of the acrylic acid. Thereafter, 0.13 g of potassium persulfate was dissolved therein. The aqueous monomer solution has 48.6 g of a solids content equivalent to the polymer and 67.1 g of a moisture amount (moisture content: 138 mass %).

The resulting aqueous solution of partially neutralized acrylate was added to the four-necked flask and dispersed. The air in the system was sufficiently purged with nitrogen again and then heated. The solution was heated and polymerized for 3 hours in a bath kept at 55° C. to 60° C. To the resulting polymerization solution was added 0.05 g (0.00029 mol) of ethylene glycol diglycidyl ether. Then, the solution was dried by distillation of water and cyclohexane to give 48.5 g of a finely granular dried polymer.

Comparative Example 3

Water-absorbing resin particles were obtained in the same manner as in Example 2, except that 7.0 mg (45 μmol) of N,N'-methylenebisacrylamide was added to the aqueous monomer solution as an internal crosslinking agent before the polymerization. The yield of the resin particles was 72.1 g.

Comparative Example 4

A 500-mL Erlenmeyer flask was charged with 92 g (1.02 mol) of an 80 mass % aqueous solution of acrylic acid, and then 146.0 g of a 21.0 mass % aqueous solution of sodium hydroxide was added dropwise thereto with cooling with ice to neutralize 75 mol % of the acrylic acid. Thus, an aqueous solution of partially neutralized acrylate having a monomer concentration of 38 mass % was prepared. To the resulting aqueous solution of partially neutralized acrylate was added 18.4 mg (106 µmol) of ethylene glycol diglycidyl ether as an internal crosslinking agent and 92 mg of potassium persulfate as a radical polymerization initiator. Thus, an aqueous monomer solution (a) for the first polymerization was prepared. A 2-L five-necked cylindrical round bottomed flask equipped with a stirrer, a two-step paddle blade, a reflux condenser, a dropping funnel, and a nitrogen gas inlet tube was charged with 340 g (500 mL) of n-heptane, and then 0.92 g of a sucrose fatty acid ester (S-370, HLB: 3.0, manufactured by Mitsubishi-Kagaku Foods Corporation) as a surfactant was dissolved in the n-heptane. Then, the temperature inside the flask was set at 35° C. Thereafter, the aqueous monomer solution (a) for the first polymerization was added thereto. The solution was kept at 35° C. and suspended with stirring, and the air in the system was purged with nitrogen. The flask was then immersed in a water bath set at 70° C. to increase the temperature. The polymerization reaction was carried out for 2 hours.

A 500-mL Erlenmeyer flask was charged with 92 g (1.02 mol) of an 80 mass % aqueous solution of acrylic acid, and then 146.0 g of a 21.0 mass % aqueous solution of sodium hydroxide was added dropwise thereto with cooling with ice to neutralize 75 mol % of the acrylic acid. Thus, an aqueous solution of partially neutralized acrylate having a monomer concentration of 38 mass % was prepared. To the resulting aqueous solution of partially neutralized acrylate was added 9.2 mg (53 µmol) of ethylene glycol diglycidyl ether as an internal crosslinking agent and 18.4 mg of potassium persulfate as a radical polymerization initiator. Thus, an aqueous monomer solution (b) for the second reversed-phase suspension polymerization was prepared. After the completion of the first reversed-phase suspension polymerization, the polymerization slurry was cooled to 50° C. Then, the aqueous monomer solution (b) for the second polymerization was added dropwise into the system in which the surfactant was dissolved. The resulting solution was stirred for 30 minutes at 50° C., and simultaneously, the air in the system was sufficiently purged with nitrogen gas. Then, the flask was immersed in a water bath set at 70° C. to increase the temperature. The polymerization reaction was carried out for 1.5 hours to give a hydrogel polymer.

Subsequently, the temperature was increased using an oil bath set at 120° C. and 250 g of water was distilled off from the system by azeotropic distillation of water and n-heptan with reflux of n-heptan. Thereafter, 110 mg (0.00063 mol) of ethylene glycol diglycidyl ether was added thereto (first drying process). At this time, the moisture content (based on polymer solid content) was 25 mass % based on the water-soluble ethylenically unsaturated monomer component constituting the hydrogel polymer. A mixture of the hydrogel polymer with a post-crosslinking agent was prepared, and the mixture was kept at 80° C. for 2 hours.

Then, the mixture was dried by evaporation of the n-heptane (second drying process) to give 188.3 g of spherical water-absorbing resin particles.

Evaluation

The water-absorbing resin particles obtained in Examples and Comparative Examples were evaluated for the following properties. Table 1 shows the results.

(1) Physiological Saline Absorption of Water-Absorbing Resin Particles

A 500-mL beaker was charged with 500 g of 0.9 mass % saline, and thereto was added 2.0 g of the water-absorbing resin particles. The mixture was stirred for 60 minutes. A mass Wa (g) of a JIS standard sieve with a mesh size of 75 µm was previously determined, and the contents of the beaker were filtered using this sieve. Then, the sieve was allowed to stand for 30 minutes in such a state that the sieve was tilted at a tilt angle of about 30 degrees to the horizontal to filter out excess water.

A mass Wb (g) of the sieve containing water-absorbed gel was determined, and the water absorption was determined by the following formula:

$$\text{Physiological saline absorption} = (Wb - Wa)/2.0$$

(2) Physiological Saline Absorption Rate of Water-Absorbing Resin Particles

This test was performed in a room at 25±1° C. A 100-mL beaker was charged with 50±0.1 g of physiological saline, a stir bar (8 mmφ×30 mm, without ring) for a magnetic stirrer is placed into the beaker, and the beaker was immersed in a thermostatic bath to adjust the temperature of the solution at 25±0.2° C. Then, the beaker was placed on a magnetic stirrer. The rotational speed was set at 600 r/min. After the formation of eddies in the physiological saline, 2.0±0.002 g of water-absorbing resin particles was quickly added to the beaker. The time (second) from the addition of the water-absorbing resin particles until the eddies on the liquid surface vanishes was measured using a stopwatch to determine the water-absorption rate of the water-absorbing resin particles.

(3) Median Particle Size of Water-Absorbing Resin Particles

With 100 g of the water-absorbing resin particles was mixed 0.5 g of amorphous silica (Sipernat 200 manufactured by Evonik Degussa Japan Co., Ltd.) as a lubricant.

The water-absorbing resin particles were allowed to pass through a JIS standard sieve with a mesh size of 250 µm. If 50 mass % or more of the resin particles passes through the sieve, a median particle size was measured using the combination (A) of sieves. On the other hand, if 50 mass or more of the resin particles was left on the sieve, a median particle size was measured using the combination (B) of sieves.

(A) JIS standard sieves were stacked in the following order, from the top, of: a sieve with a mesh size of 425 µm, a sieve with a mesh size of 250 µm, a sieve with a mesh size of 180 µm, a sieve with a mesh size of 150 µm, a sieve with a mesh size of 106 µm, a sieve with a mesh size of 75 µm, a sieve with a mesh size of 45 µm, and a saucer.

(B) JIS standard sieves were stacked in the following order, from the top, of: a sieve with a mesh size of 850 µm, a sieve with a mesh size of 600 µm, a sieve with a mesh size of 500 µm, a sieve with a mesh size of 425 µm, a sieve with a mesh size of 300 µm, a sieve with a mesh size of 250 µm, a sieve with a mesh size of 150 µm, and a saucer.

The water-absorbing resin particles were placed on the sieve at the top of the combination of the sieves and classified by shaking the sieves using a ro-tap sieve shaker for 20 minutes.

A mass of the water-absorbing resin particles left on each sieve relative to the total amount of the water-absorbing resin particles was expressed in mass percent. The resulting values were summed in the order of decreasing particle size, so that the relation between the mesh size of each sieve and the corresponding summed value of the water-absorbing resin particles left on the sieve expressed in mass percent was plotted on a logarithmic probability paper. The plotted points on the logarithmic probability paper were connected by a straight line to determine a particle size corresponding to 50 mass % integrated mass percent, which was defined as a median particle size.

(4) Swelling Capacity of Water-Absorbent Resin Particles

The swelling capacity of one minute after the start of the water absorption and the swelling capacity of 10 minutes after the start of the water absorption were determined using swelling capacity measuring apparatus. FIG. 1 is a schematic explanation view of the swelling capacity measuring apparatus. The swelling capacity measuring apparatus X shown in FIG. 1 includes travel distance measuring apparatus 1, a concave circular cup 2 (30 mm in height, 80.5 mm in inside diameter), a plastic convex circular cylinder 3 (80 mm in outside diameter, 60 through holes 7 with a diameter of 2 mm are uniformly formed in a contact face that is in contact with the water-absorbing resin particles), and a nonwoven fabric 4 (liquid permeable nonwoven fabric with a basis weight of 12 g/m$^2$). The swelling capacity measuring apparatus X can determine a change in the distance in 0.01 mm increments using a laser beam 6. The concave circular cup 2 is made so that a predetermined amount of water-absorbing resin particles is uniformly dispersed. The convex circular cylinder 3 is made so as to uniformly apply 90 g of weight to the water-absorbing resin particles 5.

0.1 g of a sample (water-absorbing resin particles 5) was uniformly dispersed in the concave circular cup 2, and the nonwoven fabric 4 was disposed thereon. The convex circular cylinder 3 is softly disposed on the nonwoven fabric 4. The travel distance measuring apparatus 1 was set so that the laser beam 6 illuminated the center portion of the cylinder. 130 g of ion exchange water previously adjusted at 20° C. was added in the concave circular cup 2, whereby the water-absorbing resin particles 5 were swollen to press the convex circular cylinder 3. The travel distance of the convex circular cylinder 3 was determined. The travel distances of the convex circular cylinder 3 after one minute from the start of the water absorption and after 10 minutes from the start of the water absorption were determined as the initial swelling capacity (value after 1 minute) and equivalent swelling capacity (value after 10 minutes), respectively. The ratio (initial swelling ratio) of the initial swelling capacity (value after 1 minute) to the equilibrium swelling capacity (value after 10 minutes) was determined.

TABLE 1

| | Amount of internal crosslinking agent [μmol] | Moisture content [mass %] | Post-crosslinking agent | | Physiological saline absorption [g/g] | Physiological saline absorption rate [sec] | Median particle size [μm] | Swelling capacity | |
| | | | Amount [mol] | Amount based on monomer [mol %] | | | | Equilibrium swelling capacity [mm] | Ratio of initial swelling capacity [%] |
| --- | --- | --- | --- | --- | --- | --- | --- | --- | --- |
| Example 1 | — | 52 | 0.00016 | 0.020 | 68 | 2 | 160 | 14.4 | 91 |
| Example 2 | — | 57 | 0.00012 | 0.015 | 67 | 3 | 150 | 13.8 | 91 |
| Example 3 | — | 71 | 0.00008 | 0.010 | 69 | 3 | 140 | 12.6 | 84 |
| Example 4 | — | 48 | 0.0002 | 0.026 | 61 | 2 | 150 | 15.1 | 88 |
| Example 5 | — | 49 | 0.00019 | 0.024 | 70 | 2 | 160 | 14.1 | 90 |
| Example 6 | — | 52 | 0.00016 | 0.020 | 66 | 3 | 220 | 12.1 | 85 |
| Example 7 | — | 52 | 0.00016 | 0.020 | 65 | 3 | 250 | 13.2 | 88 |
| Example 8 | — | 52 | 0.00016 | 0.020 | 63 | 2 | 340 | 13.2 | 88 |
| Comparative Example 1 | — | 28 | 0.00048 | 0.061 | 68 | 2 | 160 | 9.8 | 94 |
| Comparative Example 2 | — | 138 | 0.00029 | 0.053 | 90 | 2 | 150 | 8.4 | 79 |
| Comparative Example 3 | 45 | 57 | 0.00012 | 0.015 | 59 | 3 | 120 | 9.1 | 88 |
| Comparative Example 4 | 159 | 25 | 0.00063 | 0.031 | 60 | 6 | 60 | 9.8 | 67 |

Table 1 shows that the water-absorbing resin particles obtained in Examples 1 to 8 have high swelling capacity and an appropriate median particle size, but the water-absorbing resin particles obtained in Comparative Examples have insufficient swelling capacity.

INDUSTRIAL APPLICABILITY

The water-absorbing resin particles of the present invention may be widely used in various fields of, for example, hygienic articles such as disposable diaper, sanitary articles, and pet sheets; agricultural and horticultural materials such as water-retaining materials and soil conditioners; and industrial and construction materials such as water blocking materials for cables such as power cables and optical communication cables and dewfall preventing materials. Particularly, the resin particles are used for industrial and construction materials such as water blocking materials for power cables and optical communication cables.

REFERENCE SIGNS LIST

1 Travel distance measuring apparatus
2 Concave circular cup
3 Convex circular cylinder
4 Nonwoven fabric
6 Water-absorbing resin particle
6 Laser beam
7 Through hole
X Swelling capacity measuring apparatus

The invention claimed is:

1. A method for producing water-absorbing resin particles, which comprises:
    preparing a hydrogel polymer by reversed-phase suspension polymerization of a water-soluble ethylenically unsaturated monomer in a hydrocarbon solvent in the absence of an internal crosslinking agent but in the presence of a surfactant having an HLB in a range from 8 to 12; and
    carrying out a post-crosslinking reaction of the hydrogel polymer, whose moisture content has been adjusted so as to form a first-dried gel, to in a range from 30 to 110 mass % relative to a water-soluble ethylenically unsaturated monomer component that forms the hydrogel polymer,
    wherein a ratio (A:B) is in a range from 99:1 to 70:30, where A is a moisture content (A) of the first-dried gel and B is a moisture amount (B) added with a post-crosslinking agent for the post-crosslinking reaction.

2. The method according to claim 1,
    wherein the surfactant having the HLB in a range from 8 to 12 is at least one compound selected from the group consisting of sorbitan fatty acid esters, polyglycerine fatty acid esters, and sucrose fatty acid esters.

3. The method according to claim 1,
    wherein the post-crosslinking agent is a glycidyl ether compound.

4. The method according to claim 1,
    wherein an amount of the post-crosslinking agent is in a range from 0.0001 to 1 mol % relative to a total molar amount of the water-soluble ethylenically unsaturated monomer.

5. The method according to claim 1,
    wherein an amount of the post-crosslinking agent relative to a total molar amount of the water-soluble ethylenically unsaturated monomer is in a range satisfying formula (1):

$$(-0.0002Z+0.023) \leq Y \leq (-0.0002Z+0.050) \quad (1)$$

wherein Y represents an amount (mol %) of the post-crosslinking agent, and
    Z represents the moisture content (mass %) of the hydrogel polymer upon mixing with the post-crosslinking agent.

6. Water-absorbing resin particles obtained by the method according to claim 1.

7. The water-absorbing resin particles according to claim 6,
    wherein equilibrium swelling capacity of the water-absorbing resin is in a range from 10 to 28 mm,
    a water-absorption rate of the water-absorbing resin is in a range from 1 to 20 seconds, and
    a median particle size of the water-absorbing resin is in a range from 80 to 400 μm.

8. An absorbent article, which comprises:
    a liquid-permeable sheet;
    a liquid-impermeable sheet; and
    an absorber sandwiched between the liquid-permeable sheet and the liquid-impermeable sheet, the absorber including the water-absorbing resin particles according to claim 6.

9. A water blocking material, which comprises:
    two or more liquid-permeable sheets; and
    an absorber sandwiched with the two or more liquid-permeable sheets, the absorber including the water-absorbing resin particles according to claim 6 in an amount from 30 to 300 g/m².

* * * * *